United States Patent [19]

Schneider et al.

[11] Patent Number: 5,045,304

[45] Date of Patent: Sep. 3, 1991

[54] CONTRAS AGENT HAVING AN IMAGING AGENT COUPLED TO VIABLE GRANULOCYTES FOR USE IN MAGNETIC RESONANCE IMAGING OF ABCESS AND A METHOD OF PREPARING AND USING SAME

[75] Inventors: David R. Schneider, Birmingham; Kostaki G. Bis, Troy, both of Mich.

[73] Assignee: Wayne State University, Detroit, Mich.

[21] Appl. No.: 238,870

[22] Filed: Aug. 31, 1988

[51] Int. Cl.$^5$ .................. G01N 31/00; G01N 24/00; A01N 1/02; A61K 33/26

[52] U.S. Cl. ........................................ 424/9; 436/173; 435/2; 424/646; 424/647; 424/648

[58] Field of Search .................. 424/9, 647, 648; 436/173; 128/653, 653 AF, 653 CA, 654; 435/2

[56] References Cited

U.S. PATENT DOCUMENTS

| | | | |
|---|---|---|---|
| 4,269,821 | 5/1981 | Kreuter et al. | 493/89 |
| 4,452,773 | 6/1984 | Molday | 424/1.1 |
| 4,497,791 | 2/1985 | Gamble et al. | 424/1.1 |
| 4,554,088 | 11/1985 | Whitehead et al. | 252/62.54 |
| 4,612,185 | 9/1986 | Dean | 424/2 |
| 4,615,879 | 10/1986 | Runge et al. | 424/9 |
| 4,628,037 | 12/1986 | Chagnon et al. | 436/526 |
| 4,637,929 | 1/1987 | Quay | 424/9 |
| 4,639,364 | 1/1987 | Hoey | 424/9 |
| 4,669,481 | 6/1987 | Eisenberg et al. | 128/654 |
| 4,672,040 | 6/1987 | Josephson | 436/526 |
| 4,675,173 | 6/1987 | Widder | 424/9 |
| 4,687,658 | 8/1987 | Quay | 424/9 |
| 4,714,607 | 12/1987 | Klaveness | 424/9 |
| 4,729,892 | 3/1988 | Beall | 424/9 |
| 4,755,375 | 7/1988 | Srivastava et al. | 424/1.1 |
| 4,770,183 | 8/1988 | Groman et al. | 128/654 |
| 4,789,541 | 12/1988 | Davis | 424/1.1 |
| 4,935,223 | 6/1990 | Phillips | 424/1.1 |

OTHER PUBLICATIONS

Inflammatory Lesions Localized with Technetium TC99m-Labeled Leukocytes, B. Anderson, D. English, H. Akalin, W. Henderson, *Arch Intern Med.*, vol. 135, Aug. 1975, pp. 1067-1071.

Labeling of Phagocytes from Human Blood with 99m TC-Sulfur Colloid, D. English and B. Anderson, *J Nucl Med*, vol. 16, Aug. 1974, pp. 5-10.

Leukocyte Labeling with Technetium-99m Tin Colloids, B. Mack and D. English, *J Nucl Med*, vol. 28, Sep. 1987, pp. 1471-1477.

Survey of Radioactive Agents for In-Vitro Labeling of Phagocytic Leukocytes, II Particles, J. McAfee and M. Thakur, *J Nucl Med*, vol. 17, Jan. 1976, pp.488-492.

Young, IR Enhancement of Relaxation Rate with Paramagnetic Contrast Agents in NMR Imaging J. Computed Tomography 5(6): 543-6 (1981).

Eckelman, W. C., Radio Pharmaceuticals Labelled with Technetium International J. Applied Radiation & Isotopes 28:67-82 (1977).

*Primary Examiner*—Richard L. Raymond
*Assistant Examiner*—Gary E. Hollinden
*Attorney, Agent, or Firm*—Gifford, Groh, Sprinkle, Patmore and Anderson

[57] ABSTRACT

A method and contrast agent for magnetic resonance imaging (MRI) of abcesses. Granulocytes are separated from whole blood and incubated with an imaging vehicle such as magnetite. The granulocytes encapsulate the imaging vehicle and are suspended in an intravascularly administrable carrier to form the contrast agent. The contrast agent is highly specific for MRI of abcesses.

12 Claims, No Drawings

CONTRAS AGENT HAVING AN IMAGING AGENT COUPLED TO VIABLE GRANULOCYTES FOR USE IN MAGNETIC RESONANCE IMAGING OF ABSCESS AND A METHOD OF PREPARING AND USING SAME

BACKGROUND OF THE INVENTION

I. Field of the Invention

The field of this invention is that of contrast agents for magnetic resonance imaging (MRI). More specifically, this invention relates to a method and reagent for use in magnetic resonance imaging of abscess.

II. Description of the Related Art

Magnetic resonance imaging (MRI) is known as an imaging modality for diagnosing various conditions in a patient. In order to specifically image a particular tissue in the body, it is necessary to direct a contrast agent having paramagnetic or super-paramagnetic properties to the tissue to be imaged. It is known as disclosed in U.S. Pat. No. 4,729,892 to use cross-linked hydrogel materials as contrast agents for imaging gastro-intestinal tract. It is also known as disclosed in Eisenberg et al U.S. Pat. No. 4,669,481 to label red blood cells with chromium for imaging the liver or spleen. It is also known as disclosed in Eisenberg et al U.S. Pat. No. 4,669,481 to use metal chelates, such as Gd-DTPA and nitroxide stable radicals (NSFRs) as contrast agents however these agents are of limited use because of target specificity, toxicity and relatively short duration signal.

Heretofore, the ability to determine the nature of abscess in a patient has been accomplished only by computerized tomography and ultra sound. These modalities cannot distinguish an abscess from a neoplastic mass. Because of the non-invasive characteristics of magnetic resonance imaging, it would be useful to image abscess by magnetic resonance imaging. Therefore, it would be advantageous to provide a contrast agent which would target abscess and provide sufficient contrast to distinguish abscess from neoplastic mass.

SUMMARY OF THE PRESENT INVENTION

Accordingly, the present invention consists of a contrast agent for use in magnetic resonance imaging of abcess and a method of preparation and use of the contrast agent. The contrast agent consists of an imaging vehicle or agent which has been coupled to viable granulocytes. The contrast agent is administered to the patient by intraveneous infusion for imaging of abscess.

The imaging vehicle is an agent which is either para-magnetic, ferro-magnetic, or super-paramagnetic. The imaging vehicle may be formed from known paramagnetic metals such as iron, gadolinium, indium, copper, manganese, etc. The para-magnetic metals may be in the form of chelates, such as DTPA; salts; or in the form of elemental metal. The preferred imaging vehicle is magnetite, $Fe_2O_3.FeO$ which has been coated with a polymer having a high percentage of carboxyl (COOH) groups.

Granulocytes are isolated from the blood of a patient and mixed with an aqueous solution of the imaging vehicle. In the preferred embodiment, the mixture is incubated for a predetermined period of time to permit the granulocytes to encapsulate the polymer-coated magnetite. Once encapsulation has taken place, the granulocytes are labelled. Labelled granulocytes are then suspended in an intravascularly administerable liquid carrier. The labelled granulocytes may be separated from the aqueous solution. The granulocytes are examined microscopically to determine viability. The suspension of labelled granulocytes is reintroduced into the patient and a specified amount of time is allowed to pass in order for the labelled granulocytes to migrate to abcess sites. The MRI examination is then carried out in the usual manner to obtain an image of the abscess The labelled granulocytes can be observed using $T_1$, $T_2$ and mixed $T_1$ and $T_2$ weighted pulse sequences.

EXPERIMENTAL

The method of this invention was tested on an experimental basis using polymer-coated magnetite. Magnetite has a formulation of $Fe_2O_3.FeO$. The polymer-coated magnetite had a high percentage of carboxyl groups (COOH) and a molecular weight of 215.5.

A. Preparation

A commercially available carboxyl terminal polymer-coated magnetite sold by Advanced Magnetics, Inc. of Cambridge, Mass., under the trade name "Biomag" was utilized. The "Biomag" was packaged in a suspension of water, having a concentration of 268 $\mu$ moles Fe/cc. The particles were pelleted from the suspension by centrifugation. The polymer-coated magnetite was re-suspended to its original volume in Hank's physiologic buffer, available from Sigma Corporation, and prepared according to package directions (pH=7.2) in order to form a suspension of polymer-coated magnetite in Hank's physiologic buffer.

Calculations for the amount of agent needed to relax $T_1$ and $T_2$ are as follows:

10 $\mu$/moles of $Fe^{+++}$ per kilogram of tissue to be imaged are required to reduce the signal intensity of the $T_2$ weighted image by 50%. It was found that the granulocytes from 100 cc's of blood encapsulated 18.5$\mu$ moles of polymer-coated magnetite. Since 18.5 $\mu$ moles of Biomag contains $10^5$ particles $Fe^{+++}$ and 100 cc's of blood $0.5 \times 10^6$ granulocytes, each granulocyte encapsulates an average of 5 particles. By observation it was determined that a granulocyte may encapsulate as many as 8 particles of $Fe^{+++}$. Additionally, since 18.5 $\mu$ moles of $Fe^{+++}$ were encapsulated by the granulocytes from 100 cc's of blood, 1.85 kilograms of tissue could be imaged by the labelled granulocytes.

Whole blood was drawn in heparinized syringes from Sprague-Dawley rats in order to obtain 50 ccs total volume. The whole blood was then centrifuged at 400 g's for 30 minutes onto a 50% v/v Ficoll-Hypaque gradient in order to separate granulocytes from the whole blood.

The granulocytes were removed from the gradient and placed in Hank's physiologic buffer at a concentration of 200,000 granulocytes per ml.

A solution of 3% Hydroxyethyl Starch (HES) was prepared to facilitate aggregation of the granulocytes. The HES was added to the granulocytes in Hank's physiologic buffer at a concentration of 1 ml HES to 10 ml granulocytes in Hank's physiologic buffer, to form solution of granulocytes and HES in Hank's physiologic buffer.

B. RAT IMAGING

Four Sprague-Dawley rats weighing between 428 and 482 gm were injected with 0.2 ml of sterile turpentine into the right hind leg, according to the procedure described in "Preparation and Evaluation of $^{111}$In-labeled Leukocytes as an Abcess Imaging Agent in Dogs", Thakur et al, Radiology 119: 731-732, June, 1976, in order to artificially create a sterile abcess site. After 24 hours, baseline MR images of the sites were obtained for each of the four rats.

The solution of prepared granulocytes in Hank's physiologic buffer was mixed with polymer-coated magnetite (BIOMAG) in Hank's physiolgic buffer at a ratio of 1 ml granulocytes in Hank's physiologic buffer to 0.1 ml polymer-coated magnetite in Hank's physiologic buffer, to form a coupled solution in which the metal binds to and is subsequently incorporated into the granulocytes.

As known in the art, the coupled solution was incubated with $O_2$ bubbling through at 37 degrees C. for thirty to sixty minutes. The specified length of time was determined by observation of the speed with which the granulocytes encapsulate or phagatacize one to four particles of polymer-coated magnetite. Encapsulation was visually assessed using a microscope and by staining an aliquot of the granulocytes with an iron stain and/or Wright's stain using standard procedures.

Encapsulation was completed after one to eight polymer-coated magnetite particles had been encapsulated by the majority of viable granulocytes. The average encapsulation time is 30 to 60 minutes The granulocytes containing the polymer-coated magnetite were considered labelled, and could be separated from the coupled solution if required using a pole magnet smaller in volume than the mixing vessel in order to isolate the labelled granulocytes, or contrast agent.

The contrast agent was then injected into each rat at a concentration of 200,000 labelled granulocytes per rat. The rats were imaged after 30 minutes to 24 hours, in order for the granulocytes to migrate to the abscess sites.

C. RESULTS

Rats were imaged using $T_1$, $T_2$ and mixed $T_1$ and $T_2$ weighted pulse sequences. Images were compared to baseline.

DETAILED DESCRIPTION OF THE PREFERRED EMBODIMENT

According to the invention, the contrast agent for magnetic resonance imaging of abcess is formed by coupling an imaging vehicle to granulocytes isolated from whole blood. The imaging vehicle may be either para- and ferro-magnetic in the form of $Fe_2O_3.XO$, where X is one of the known paramagnetic metals, such as iron, gadolinium, indium, copper, or manganese. The paramagnetic metals may be in the form of chelates, such as DTPA, salts, or elemental metal.

The preferred embodiment for the contrast agent is a suspension of granulocytes which have encapsulated or phagocytised polymer-coated magnetite. According to the method of the invention, the suspension is formed in the manner disclosed in the experimental section above.

In the preferred embodiment, the imaging vehicle is polymer-coated magnetite, magnetite being $Fe_2O_3.FeO$. The magnetite is coated with polymer to facilitate encapsulation by the granulocytes. The magnetite is coated with a polymer of carbon-link chains having functional terminal groups consisting of carboxyl (COOH), amine (NH2) or other functional chemicals. A suitable polymer-coated magnetite is available from Advance Magnetics, Inc. of Cambridge, Mass., and sold under the trade name "Biomag". BIOMAG is available in a suspension of water having a concentration of 268 $\mu$ moles Fe/cc and a molecular weight of 215.5. The water was removed from the suspension by centrifugation, as is known in the art. The particles of polymer-coated magnetite were re-suspended in 0.1 to 0.5 ml of Hank's physiologic buffer. Hank's physiologic buffer is available from Sigma Corporation, and the suspension was prepared according to package directions (pH=7.2) to form a suspension of polymer-coated magnetite (BIOMAG particles) in Hank's physiologic buffer.

A supply of the granulocytes is then isolated from whole blood. In the preferred embodiment, whole blood is drawn from the person or animal whose tissue is to be imaged. Whole blood is drawn in heparinized syringes to obtain a suitable supply of granulocytes. 500,000 granulocytes may be isolated from 100 cc's of blood. The 500,000 granulocytes will encapsulate 1.85 $\mu$ moles of Biomag to produce a sufficient quantity of contrast agent to image 1.85. kilograms of tissue.

A supply of heparinized blood is then mixed with a 3% Hydoxyethyl Starch (HES) solution, available from McGraw Laboratories, Chicago, Ill. The solution is formed in a ratio of 100 cc's of blood to 20 cc's of the 3% HES. The solution is permitted to stand for 30 to 60 minutes to an hour and a half. The HES solution facilitates aggregation of the granulocytes as the red blood cells will rouleaux, as known in the art. The serum containing the granulocytes is then drawn off from the rouleauxed blood and centrifuged at 250 g's for five minutes. The granulocytes are then removed by suitable means such as pipetting and re-suspended in a 1 to 2 mls volume Hank's physiologic buffer.

The Hank's solution containing the imaging vehicle (I), is combined with a solution of granulocytes in Hank's (II) at a ratio of 0.1 to 0.5 ml (I) to 1 to 2 ml (II), thus forming a coupled solution. The coupled solution is then incubated at 37° C. The coupled solution is oxygenated by blowing $O_2$ on the surface of the solution during incubation in order to preserve the viability of the granulocytes. The granulocytes encapsulate or phagocytise a polymer-coated magnetite in 30 to 60 minutes. After 30 minutes, approximately 90% of the granulocytes will have encapsulated at least 3 particles of polymer-coated magnetite. By 60 minutes, each of the granulocytes has encapsulated or phagacytized 3 to 8 particles. The labelled granulocytes may be separated from the aqueous solution of physiologic buffer in unlabelled granulocytes. One method of separation is inserting a pole magnet smaller than the vessel containing the coupled solution to attract the labelled granulocytes. However, since 90% of the granulocytes successfully encapsulate the polymer-coated magnetite particles, it is often not necessary to separate the labelled granulocytes from the non-labelled granulocytes. Encapsulation may be visually accessed by using a microscope and by staining an aliquot of the granulocytes with an iron stain and/or Wright's stain using known procedures.

Viable labelled granulocytes are then separated from the solution, washed of debris and re-suspended in an intervasculatory admissable carrier such as plasma or physiological saline to form a contrast agent. The contrast agent must be administered within a few hours of preparation in order to insure the viability of the granulocytes. The contrast agent is suspended in a suitable equipped carrier and is administered to the patient or animal to be imaged by intravenous infusion. The same techniques and procedures may be followed as are used in the regular administration of blood. Time is permitted to elapse in order to permit the granulocytes to travel to the tissue to be imaged. This length of time is normally in the range of approximately 30 minutes to 24 hours. After the waiting period has elapsed, the patient is subjected to a standard MRI examination.

The MRI examination is carried out in a known manner with respect to the particular purpose of the examination. In general, the post sequences will be selected to maximize either contrast induced changes in $T_1$ or $T_2$. $T_1$ and $T_2$ current tissue primers to determine saline intensity of MRI imaging. The appearance of a sharply delineated dark area in the tissue is interpreted to be a highly specific image of the abcess. Thus, abcess can be distinguished from neoplastic mass by observing a decrease in signal intensity in $T_2$ weighted images.

It is contemplated that other reagents may be formed in accordance with the invention. Isolated granulocytes may be coupled with other imaging vehicles such as paramagnetic metals such as iron, gadolinium, indium, copper, manganese, etc. These paramagnetic metals may be coupled to the granulocytes by phagocytation, studding or other suitable manners of coupling.

It should be apparent to one having ordinary skill in the art that many modifications or changes can be made to the preferred embodiment without departing from the spirit of the present invention as expressed in the scope of the appended claims.

We claim:

1. A method of preparing and using contrast agent in magnetic resonance imaging abscesses in a patient comprising the steps of:

mixing a specific number of viable granulocytes with an aqueous solution of a metallic imaging agent in which said imaging agent binds to and is subsequently incorporated into the granulocytes incubating said aqueous solution to encapsulate said imaging agent in said granulocytes to form labeled granulocytes;

separating said labeled granulocytes from said solution;

suspending said labeled granulocytes in an intravascularly administerable carrier to form said contrast agent;

administering a diagnostically effective amount of said contrast agent by intravenous infusion to said patient; and subjecting said patient to examination by magnetic resonance imaging.

2. The method of claim 1 wherein said separating step further comprises attracting said labelled granulocytes from said aqueous solution with a pole magnet.

3. The method of claim 1 further comprising after the separating step, the step of washing the labelled granulocytes with a physiologic buffer.

4. The method of claim 1 in which said imaging agent is a ferromagnetic metal or non-toxic salt thereof.

5. The method of claim 1 in which said imaging agent is a paramagnetic metal or non-toxic salt thereof.

6. The method of claim 1 in which said imaging agent is a superparamagnetic metal or non-toxic salt thereof.

7. The method of claim 1 in which said imaging agent is magnetite; $Fe_2O_3.FeO$.

8. The method of claim 1 in which the incubating step further comprises bubbling $O_2$ through said aqueous solution.

9. The method of claim 1 in which the imaging agent has the formula $F_2O_3.XO$, where X is one of the group consisting of para-magnetic and ferro-magnetic material.

10. A contrast reagent for MRI of abscesses, said reagent comprising:

a suspension of labelled granulocytes in an intravascularly adminstrable carrier, said granulocytes binding to and subsequently incorporating within a diagnostically effective amount of an imaging agent, said agent having the formula $Fe_2O_3.XO$ where X is one of the group consisting of para-magnetic and ferro-magnetic materials.

11. The contrast agent of claim 10 wherein said imaging agent is magnetite; $Fe_2O_3.FeO$.

12. The contrast agent of claim 10 wherein said intravascularly adminsterable carrier is plasma.

* * * * *

UNITED STATES PATENT AND TRADEMARK OFFICE
CERTIFICATE OF CORRECTION

PATENT NO. : 5,045,304

DATED : September 3, 1991

INVENTOR(S) : David R. Schneider
Kostaki G. Bis

It is certified that error appears in the above-identified patent and that said Letters Patent is hereby corrected as shown below:

On the title page: delete "CONTRAS" and insert --CONTRAST--;
delete "ABCESS" and insert --ABSCESS--.

Column 1, line 2, in the title, delete "Contras" and insert --Contrast--;
Column 1, line 46, delete "abcess" and insert --abscess--.

Column 2, line 7, delete "abcess" and insert --abscess--;

Column 5, line 31, Claim 1, after "using" insert --a--.
Column 5, line 32, Claim 1, after "imaging" insert --of--.

Signed and Sealed this

Twentieth Day of April, 1993

Attest:

MICHAEL K. KIRK

*Attesting Officer*  Acting Commissioner of Patents and Trademarks